: US 7,296,892 B2
(45) Date of Patent: Nov. 20, 2007

(12) United States Patent
Hanaki et al.

(54) OCULAR ACCOMMODATIVE FUNCTION EXAMINATION APPARATUS

(75) Inventors: Miwako Hanaki, Gamagori (JP); Naoki Isogai, Nishio (JP); Akihiro Hayashi, Toyokawa (JP)

(73) Assignee: Nidek Co., Ltd., Gamagori (JP)

( * ) Notice: Subject to any disclaimer, the term of this patent is extended or adjusted under 35 U.S.C. 154(b) by 401 days.

(21) Appl. No.: 11/015,417

(22) Filed: Dec. 20, 2004

(65) Prior Publication Data
US 2005/0174536 A1 Aug. 11, 2005

(30) Foreign Application Priority Data
Dec. 22, 2003 (JP) ............................. 2003-425965

(51) Int. Cl.
*A61B 3/00* (2006.01)
(52) U.S. Cl. ...................... 351/200; 351/202; 351/209; 351/210; 351/246; 351/211
(58) Field of Classification Search ......... 351/200–247
See application file for complete search history.

(56) References Cited

U.S. PATENT DOCUMENTS 5,463,430 A * 10/1995 Isogai et al. ............... 351/208
6,120,461 A *  9/2000 Smyth ....................... 600/558
6,361,168 B1 *  3/2002 Fujieda ...................... 351/208

FOREIGN PATENT DOCUMENTS

JP          2003070740 A   *  3/2003
JP          A 2003-070740      3/2003

OTHER PUBLICATIONS

Suzuki et al., "Evaluation of Accommodative Function by High Frequency Component of Accomodative Microfluctuation," *Jpn. J. Vis. Sci.*, vol. 22, No. 3, pp. 93-97 (Nov. 8, 2001).

* cited by examiner

*Primary Examiner*—Scott J. Sugarman
*Assistant Examiner*—James R Greece
(74) *Attorney, Agent, or Firm*—Oliff & Berridge, PLC

(57) ABSTRACT

An ocular accommodative function examination apparatus for examining an accommodative function of an examinee's eye, comprises: a fixation target presenting optical system which presents a fixation target at a presenting position to the eye, the presenting position being changeable in a direction of a visual axis of the eye; a refractive power measuring optical system which measures refractive power of the eye and includes a light projecting optical system which includes a light source and projects examination light to a fundus of the eye and a light receiving optical system which includes a light receiving element and receives the examination light reflected from the fundus; an analysis part which acquires variation in the refractive power of the eye gazing at the fixation target at a certain presenting position within a predetermined time based on output of the light receiving element, and determines the accommodative function including a range of accommodation and HFC (a frequency of occurrence of a high frequency component of accommodative microfluctuation) of the eye based on an acquired result; and an output part which outputs a result determined by the analysis part, wherein the analysis part determines presence/absence of accommodative constriction and presence/absence of accommodative spasm based on the determined range of accommodation and HFC.

14 Claims, 6 Drawing Sheets

OCULAR ACCOMMODATIVE FUNCTION EXAMINATION APPARATUS

BACKGROUND OF THE INVENTION

1. Field of the Invention

The present invention relates to an ocular accommodative function examination apparatus for examining an accommodative function of an examinee's eye.

2. Description of Related Art

When refractive power of an eye of an examinee who gazes at a target is objectively observed with time, the refractive power exhibits fluctuation like a sine wave, called accommodative microfluctuation. This accommodative microfluctuation is separated into a high frequency component (1.0 Hz-2.3 Hz) and a low frequency component (less than 0.6 Hz). In recent years, attention has been given to that the "a frequency of occurrence of the high frequency component" (hereinafter, HFC) of the accommodative microfluctuation has certain correlation with the degree of accommodative constriction (inertia of accommodation); e.g., the HFC increases as a burden (constriction) on the ciliary muscle becomes larger. Based on this point of view, there has been proposed a method for examining the degree of the accommodative constriction by examining the HFC (see "Evaluation of accommodative function by HFC of accommodative microfluctuation", Visual Science, Vol. 22 No. 3). Because it is thought that accommodation abnormal is one of causes of asthenopia, knowing the degree of the accommodative constriction is meaningful.

SUMMARY OF THE INVENTION

The present invention has been made in view of the above circumstances and has an object to provide an ocular accommodative function examination apparatus capable of efficiently and precisely examining an accommodative function of an eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To solve the above problems, according to the invention, there is provided an ocular accommodative function examination apparatus for examining an accommodative function of an examinee's eye, comprising: a fixation target presenting optical system which presents a fixation target at a presenting position to the eye, the presenting position being changeable in a direction of a visual axis of the eye; a refractive power measuring optical system which measures refractive power of the eye and includes a light projecting optical system which includes a light source and projects examination light to a fundus of the eye and a light receiving optical system which includes a light receiving element and receives the examination light reflected from the fundus; an analysis part which acquires variation in the refractive power of the eye gazing at the fixation target at a certain presenting position within a predetermined time based on output of the light receiving element, and determines the accommodative function including a range of accommodation and HFC (a frequency of occurrence of a high frequency component of accommodative microfluctuation) of the eye based on an acquired result; and an output part which outputs a result determined by the analysis part, wherein the analysis part determines presence/absence of accommodative constriction and presence/absence of accommodative spasm based on the determined range of accommodation and HFC.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
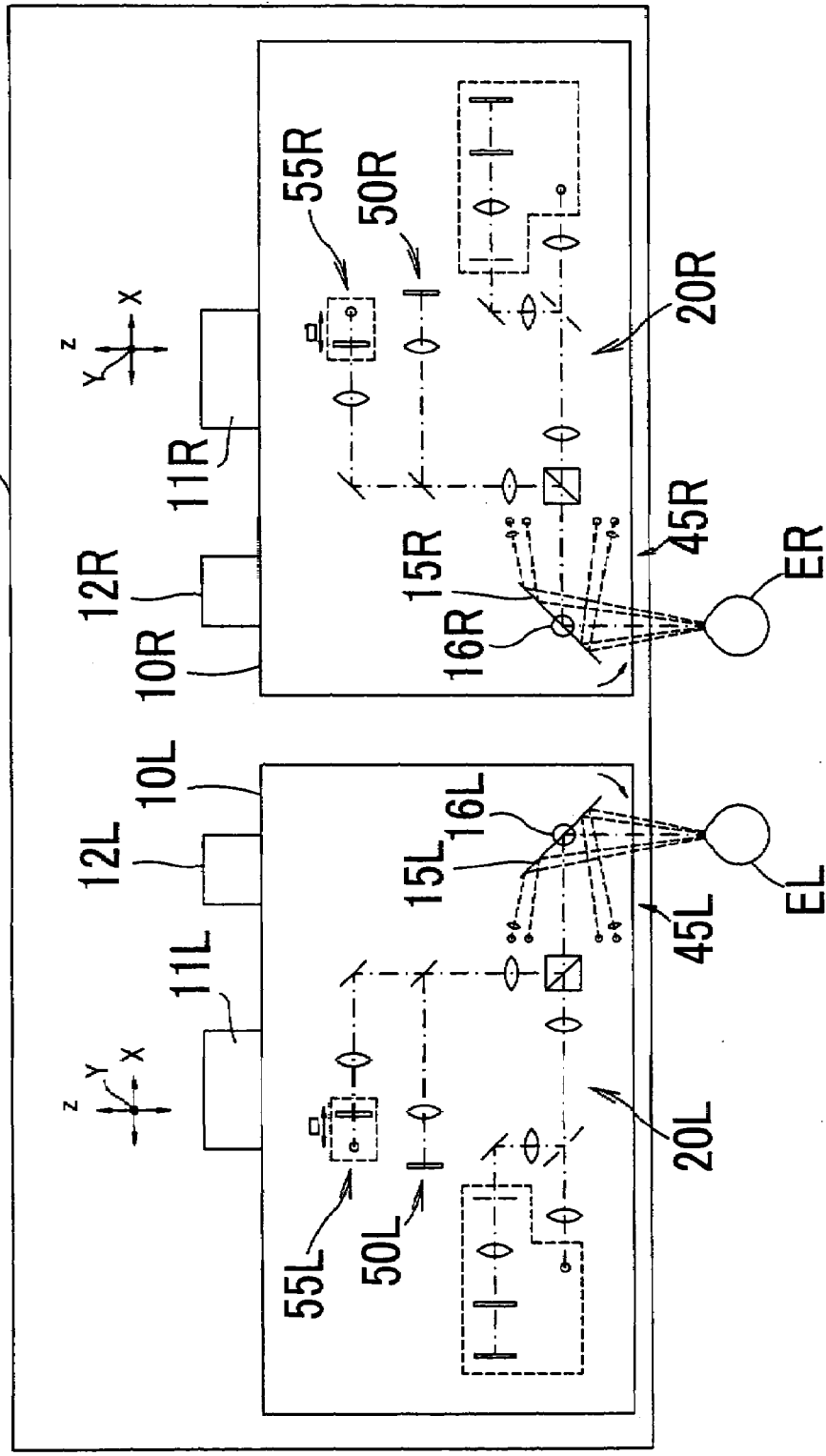
FIG. 1 is a schematic structural view of an ocular accommodative function examination apparatus.

A detailed description of a preferred embodiment of the present invention will now be given referring to the accompanying drawings. FIG. 1 is a schematic structural view of an ocular accommodative function examination apparatus in the embodiment of the invention. This apparatus is capable of simultaneously examining (measuring) both eyes.

The apparatus is provided with a right-eye examination unit 10R in which an optical system for examining a right eye ER of an examinee is disposed and a left-eye examination unit 10L in which an optical system for examining a left eye EL of the examinee is disposed. The examination unit 10R is mounted on a fixed base 2 so that it is movable in three dimensional directions; a right-and-left direction (X-direction), an up-and-down direction (Y-direction), and a back-and-forth direction (Z-direction) with respect to the eye ER. The examination unit 10L is mounted to be movable in three dimensional directions with respect to the eye EL. A moving part 11R moves the examination unit 10R in the three dimensional directions, while a moving part 11L moves the examination unit 10L in the three dimensional directions. Each of the moving parts 11R and 11L is constructed of a sliding mechanism, a motor, and others for movement in each direction. The examination units 10R and 10L may be arranged to be movable in the three dimensional directions in a suspended state from an arm or the like. A position detecting part 12R detects the position of the examination unit 10R in the three dimensional directions, while a position detecting part 12L detects the position of the examination unit 10L in the three dimensional directions. Detected positional information is utilized for detection of a pupillary distance between the eyes ER and EL, and others.

In the examination unit 10R, an eye refractive power measuring optical system 20R, an alignment target projecting optical system 45R, an observation optical system 50R which is also used for alignment target detection, a fixation target presenting optical system 55R, and a movable mirror 15R are disposed. In the examination unit 10L, an eye refractive power measuring optical system 20L, an alignment target projecting optical system 45L, an observation optical system 50L which is also used for alignment target detection, a fixation target presenting optical system 55L, and a movable mirror 15L are disposed.

Figure 2:
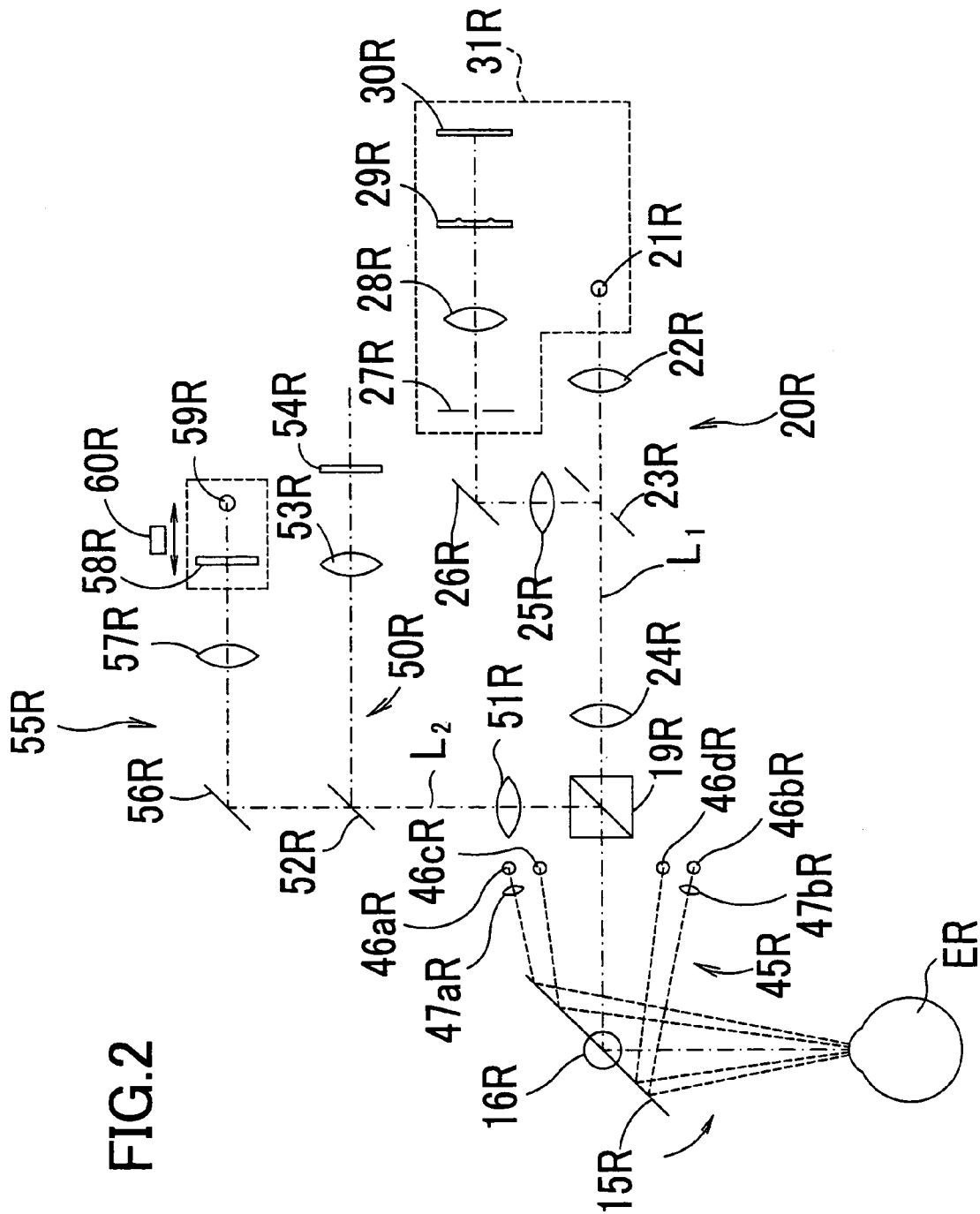
FIG. 2 is a schematic structural diagram of optical systems disposed in a right-eye examination unit.

FIG. 2 is a schematic structural view of optical systems disposed in the examination unit 10R. The measuring optical system 20R includes a light projecting optical system which projects spot-shaped examination (measurement) light to a fundus through the center portion of the pupil of the eye ER and a light receiving optical system which receives the examination light reflected from the fundus through the peripheral portion of the pupil.

The light projecting optical system includes an infrared point light source 21R such as LED, SLD, or the like, a relay lens 22R, a hole mirror 23R, and an objective lens 24R for examination (measurement), which are disposed on an optical axis L1. The light source 21R is in an optically and substantially conjugate positional relation with the fundus of the emmetropic eye ER. A hole portion of the mirror 23R is in an optically and substantially conjugate positional relation with the pupil of the eye ER. The mirror 15R is placed in front of the eye ER. A dichroic mirror (or a half mirror) 19R is disposed between the mirror 15R and the lens 24R. The mirror 19R has the property of reflecting visible light and near-infrared light while allowing infrared light to pass therethrough, thereby guiding near-infrared reflection light from an anterior segment of the eye ER to the observation optical system 50R by reflection, guiding visible fixation target light from the fixation target presenting optical system 55R (a light source 59R) to the eye ER by reflection, and guiding infrared examination light from the light projecting optical system (the light source 21R) to the eye ER by transmission.

The light receiving optical system uses the lens 24R and the mirror 23R in common with the light projecting optical system and includes a relay lens 25R and a reflection mirror 26R, which are disposed on the optical axis L1 in a reflecting direction of the mirror 23R, a light receiving diaphragm 27R, a collimator lens 28R, a ring lens 29R, and an image pick-up element 30R which is a two-dimensional light-receiving element such as a CCD or the like, which are disposed on the optical axis L1 in a reflecting direction of the mirror 26R. The diaphragm 27R and the image pick-up element 30R are in an optically and substantially conjugate positional relation with the fundus of the eye ER.

The ring lens 29R is constructed of a lens part having a cylindrical lens formed in a ring shape on one side of a transparent flat plate and a shielding part formed of shielding coating applied to the one side other than the ring shaped cylindrical lens part. With this construction, the lens 29R is formed with a ring-shaped aperture. The ring-shaped aperture of the lens 29R is in an optically and substantially conjugate positional relation with the pupil of the eye ER. On this account, the examination light reflected from the fundus is taken out, through the peripheral portion of the pupil, in a ring shape by the lens 29R (the ring-shaped aperture). When parallel light enters in the lens 29R, a ring image of the same size with the ring-shaped aperture is formed on the image pick-up element 30R disposed in a focal position of the lens 29R. The lens part and the shielding part of the lens 29R may be constructed of separate members.

The light source 21R of the light projecting optical system and the diaphragm 27R, lens 28R, lens 29R, and image pick-up element 30R of the light receiving optical system are integrally movable as a movable unit 31R along the optical axis L1. This movable unit 31R is moved according to a spherical refractive error (a spherical refractive power) of the eye ER to correct the spherical refractive error, so that the light source 21R, diaphragm 27R, and image pick-up element 30R are brought in an optically and substantially conjugate positional relation with respect to the fundus. The movement position of the movable unit 31R is detected by a potentiometer. The mirror 23R and the lens 29R are disposed to establish an optically and substantially conjugate positional relation with the pupil at a fixed magnification, independently of the movement amount of the movable unit 31R.

The alignment target projecting optical system 45R includes two first projecting optical systems disposed symmetrically with respect to the optical axis L1 and two second projecting optical systems disposed symmetrically with respect to the optical axis L1 at a smaller angle than the first projecting optical systems. The first projecting optical systems have near-infrared point light sources 46aR and 46bR such as an LED or the like and collimator lenses 47aR and 47bR and project an infinite alignment target to the eye ER by substantially parallel light. On the other hand, the second projecting optical systems have near-infrared point light sources 46cR and 46dR such as an LED or the like and project a finite alignment target to the eye ER by divergent light.

The observation optical system 50R includes an objective lens 51R for observation, a dichroic mirror (or a half mirror) 52R having the property of reflecting near-infrared light while allowing visible light to pass therethrough, a photographing lens 53R, and an image pick-up element 54R such as a CCD or the like, which are disposed on an optical axis L2 made coaxial with the optical axis L1 by the mirror 19R. An image of the anterior segment of the eye ER formed by near-infrared light source not shown for illumination of the anterior segment is formed on an image pick-up surface of the image pick-up element 54R via the mirror 15R through the lens 53R and then displayed as an observation image on a monitor 7 mentioned later. The observation optical system 50R is also used as an optical system for detecting an alignment target image formed on the cornea of the eye ER.

The fixation target presenting optical system 55R uses the lens 51R and the mirror 52 in common with the observation optical system 50R and includes a visible light source 59R, a fixation target plate 58R, a light-projection lens 57R, and a reflection mirror 56R, which are disposed on the optical axis L2 in a transmitting direction of the mirror 52R. The light source 59R and the fixation target plate 58R are moved along the optical axis L2 to optically change a presenting position (a presenting distance) of a fixation target along the visual axis of the eye ER. At the time of measurement of eye refractive power, fogging is applied for removing accommodation of the eye ER. Fixation target light provided by illumination of a fixation target (a stimulating target) of the fixation target plate 58R by the light source 59R is projected to the eye ER via the lens 57R through the mirror 15R. Thus, the eye ER can perform fixation. Instead of moving the light source 59R and the fixation target plate 58R, the lens disposed on the optical axis L2 may be moved along the optical axis L2.

The mirror 15R is rotated by a motor 16 according to convergence of the eye ER for near view, thereby changing a direction of light to be projected to the eye ER and light reflected from the eye ER.

Since the examination units 10R and 10L are basically symmetrical, the construction of the optical systems disposed in the examination unit 10L corresponds to that in the examination unit 10R by changing the reference numerals of optical members and others from "R" to "L" and therefore its explanation is omitted. The fixation target plate 58R of the examination unit 10R and the fixation target plate 58L of the examination unit 10L have identical fixation targets. Consequently, even in a simultaneous binocular examination (measurement), an examinee can view the simultaneously presented fixation targets as a single fixation target by fusion.

Figure 3:
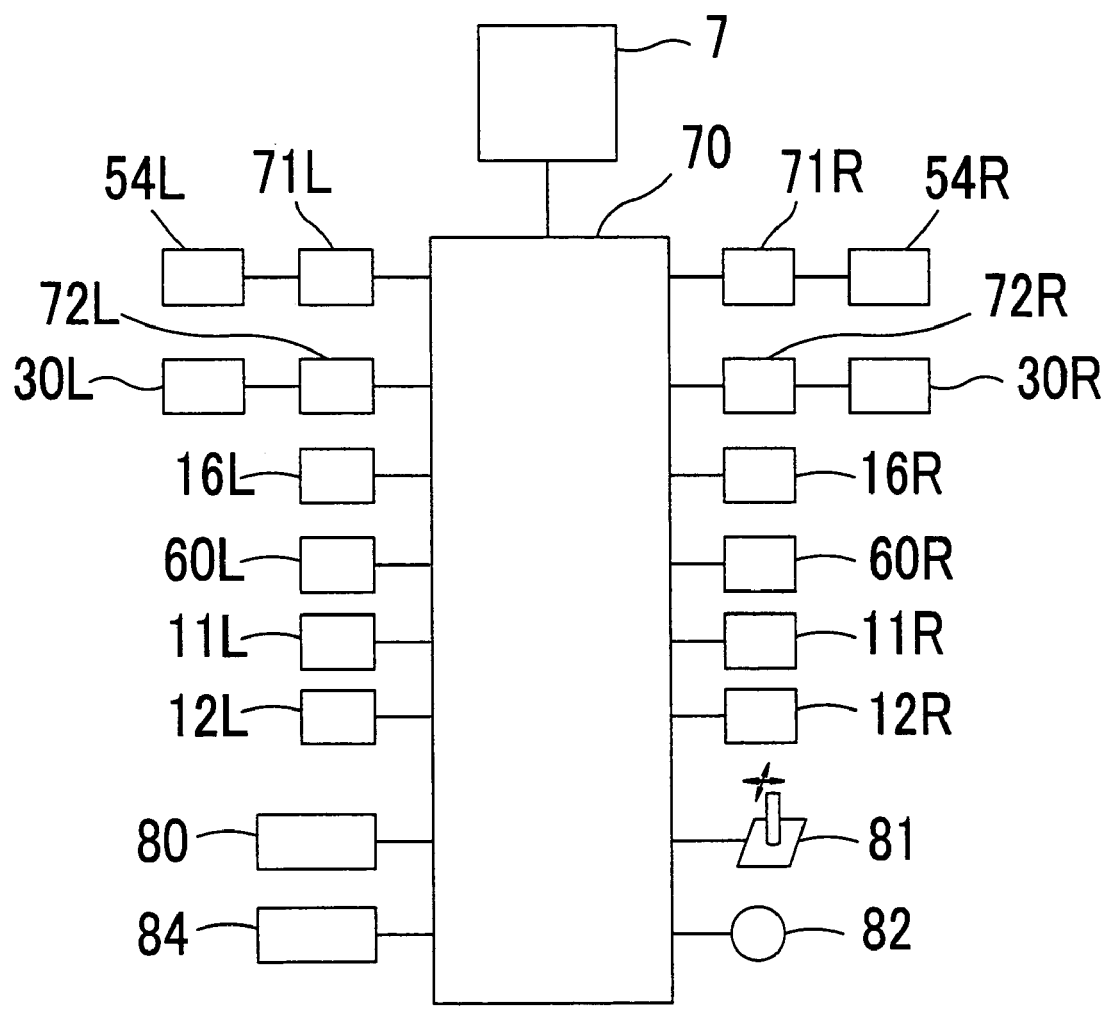
FIG. 3 is a schematic block diagram of a control system of the examination apparatus.

FIG. 3 is a schematic block diagram of a control system of the apparatus. An output signal (an image signal) from the image pick-up element 54R is inputted to an analysis and control part 70 through an image processing part 71R. An output signal (an image signal) from the image pick-up element 54L is inputted to the analysis and control part 70 through an image processing part 71L. The analysis and control part 70 detects an alignment state (positional information) of the examination unit 10R with respect to the eye ER based on an alignment target image detected and processed in the image processing part 71R and detects an alignment state (position information) of the examination unit 10L with respect to the eye EL based on an alignment target image detected and processed in the image processing part 71L. On the monitor 7, the anterior segment images of the eyes ER and EL picked up by the image pick-up elements 54R and 54L are displayed selectively or in two screens. An output signal (an image signal) from the image pick-up element 30R is inputted to the analysis and control part 70 through an image processing part 72R. An output signal (an image signal) from the image pick-up element 30L is inputted to the analysis and control part 70 through an image processing part 72L. The analysis and control part 70 obtains refractive power of the eye ER based on a ring image detected and processed in the image processing part 72R and obtains refractive power of the eye EL based on a ring image detected and processed in the image processing part 72L. Further, the analysis and control part 70 is connected to a moving part 60R which moves the light source 59R and the fixation target plate 58R along the optical axis L2, a moving part 60L which moves the light source 59L and the fixation target plate 58L along the optical axis L2, a motor 16R which rotates the mirror 15R, a motor 16L which rotates the mirror 15L, the moving parts 11R and 11L, the position detecting parts 12R and 12L, a switch part 80 including various input switches, a joystick 81 serving as operating means for moving the examination units 10R and 10L in the X- and Z-directions, a rotary knob 82 serving as operating means for moving the examination units 10R and 10L in the Y-direction, a memory 84, and others.

The examination of an accommodative function using the apparatus constructed as above is explained. The examinee rests his head on a head support unit not shown. After that, the examination unit 10R is aligned to the eye ER and the examination unit 10L is aligned to the eye EL, respectively. This embodiment exemplifies the case where an automatic alignment mode and an automatic tracking mode are selected.

Firstly, regular measurement for distance refractive power is executed. While observing images of the anterior segments of the eyes ER and EL both displayed on the monitor 7, an examiner operates the joystick 81 and the rotary knob 82 to move the examination units 10R and 10L in the X-, Y-, and Z-directions by the moving parts 11R and 11L for rough alignment. The examination units 10R and 10L are arranged to be simultaneously or separately moved. For separate movement, a separate movement mode is set by the switch on the switch part 8.

When four alignment target images formed by the alignment target projecting optical system 45R are picked up by the image pick-up element 54R, the automatic alignment and the automatic tracking of the examination unit 10R with respect to the eye ER are performed. The analysis and control part 70 determines whether an alignment state of the examination unit 10R with respect to the eye ER in the X- and Y-directions is proper based on a result of the detection of each target image. The determination of the alignment state in the X- and Y-directions is conducted by a comparison between the center position of two infinite target images formed by the first projecting optical systems and the position of the optical axis L1.

The determination of the alignment state in the Z-direction is executed by a comparison between an image distance of two infinite target images formed by the first projecting optical systems and an image distance of two finite target images formed by the second projecting optical systems. In the case of projection of a target at infinite, an image distance (image height) remains unchanged even when a working distance (a distance in the Z-direction) is changed. In the case of projection of a target at finite, on the other hand, an image distance (image height) changes according to changes in working distance. This characteristics may be utilized to determine an alignment state in the Z-direction (see U.S. Pat. No. 5,463,430 corresponding to Japanese unexamined patent publication No. H6(1994)-46999).

Likewise, when four alignment target images formed by the alignment target projecting optical system 45L are picked up by the image pick-up element 54L, the automatic alignment and the automatic tracking of the examination unit 10L with respect to the eye EL are performed. The analysis and control part 70 determines whether an alignment state of the examination unit 10L with respect to the eye EL in the X-, Y-, and Z-directions is proper based on a result of the detection of each target image.

In the above alignment, by the fixation target presenting optical systems 55R and 55L, the fixation target of the fixation target plate 58R is presented to the right eye ER and simultaneously the fixation target of the fixation target plate 58L is presented to the left eye EL. In the distance refractive power measurement, the mirrors 15R and 15L are not rotated, so that the visual axes of the eyes ER and EL are guided forward in parallel.

The analysis and control part 70 drivingly controls the moving parts 11R and 11L based on results of the determination of the alignment states in the X-, Y-, and Z-directions to move the examination units 10R and 10L in respective directions. When all of the alignment states in the above directions fall within a predetermined allowable range (proper range), the analysis and control part 70 automatically generates a trigger signal to start measurement (the examiner may input the trigger signal by pressing a measurement start switch not shown).

The examination light from the light source 21R is projected to the fundus of the eye ER via the lens 22R through the mirror 15R, and forms a spot image of the point light source on the fundus. The light of the point light source image formed on the fundus is reflected and scattered to exit from the eye ER and is reflected by the mirror 15R. After that, the light is condensed by the lens 24R and, via the mirror 23R through the mirror 26R, condensed again on an aperture of the diaphragm 27R, made into substantially parallel light by the lens 28R, made into ring-shaped light by the lens 29R, and received by the image pick-up element 30R. The picked ring image is inputted in the image processing part 72R.

The analysis and control part 70 determines the refractive power based on the ring image picked up in preliminary measurement. Further, based on the refractive power, the analysis and control part 70 moves the light source 59R and the fixation target plate 58R along the optical axis L2, bringing the fundus and the fixation target plate 58R in substantially conjugate relation, and then applies a fogging to the eye ER by moving to a far position by an appropriate diopter and determines distance refractive power based on the ring image picked up in this state. Specifically, each value of the eye ER; S (spherical power), C (cylindrical power), and A (astigmatic axis angle) is determined based on the size and shape of the ring image and the positional information of the movable unit 31R and is stored in the memory 84.

In the examination unit 10L, similarly, each value of the eye EL; S, C, and A is determined and stored in the memory 84.

After the distance refractive power measurement, continuously, the examination of an accommodative function is conducted. On the basis of the position of an S value (which can be regarded as a far point of the eyes ER and EL) of each distance refractive power of the eyes ER and EL, a presenting position of a fixation target is changed (moved) to a far position by +0.5D. Variations in refractive power within a predetermined time T (e.g., 20 seconds) at this presenting position are acquired. Thereafter, the presenting position of each fixation target is simultaneously changed (moved) in steps of 0.5D in turn to eight positions toward a near potion; +0.5D, 0.0D, −0.5D, −1.0D, −1.5D, −2.0D, −2.5D, and −3.0D. Variations in refractive power within the time T at each presenting position are acquired. The acquired variations in each refractive power are stored in the memory 84 in one-to-one correspondence with the presenting positions.

Herein, in association with the change (movement) of the presenting position of each fixation target to the near position, the mirrors 15R and 15L are rotated by an amount corresponding to the convergence amount of the eyes ER and EL at each presenting position.

Figure 4:
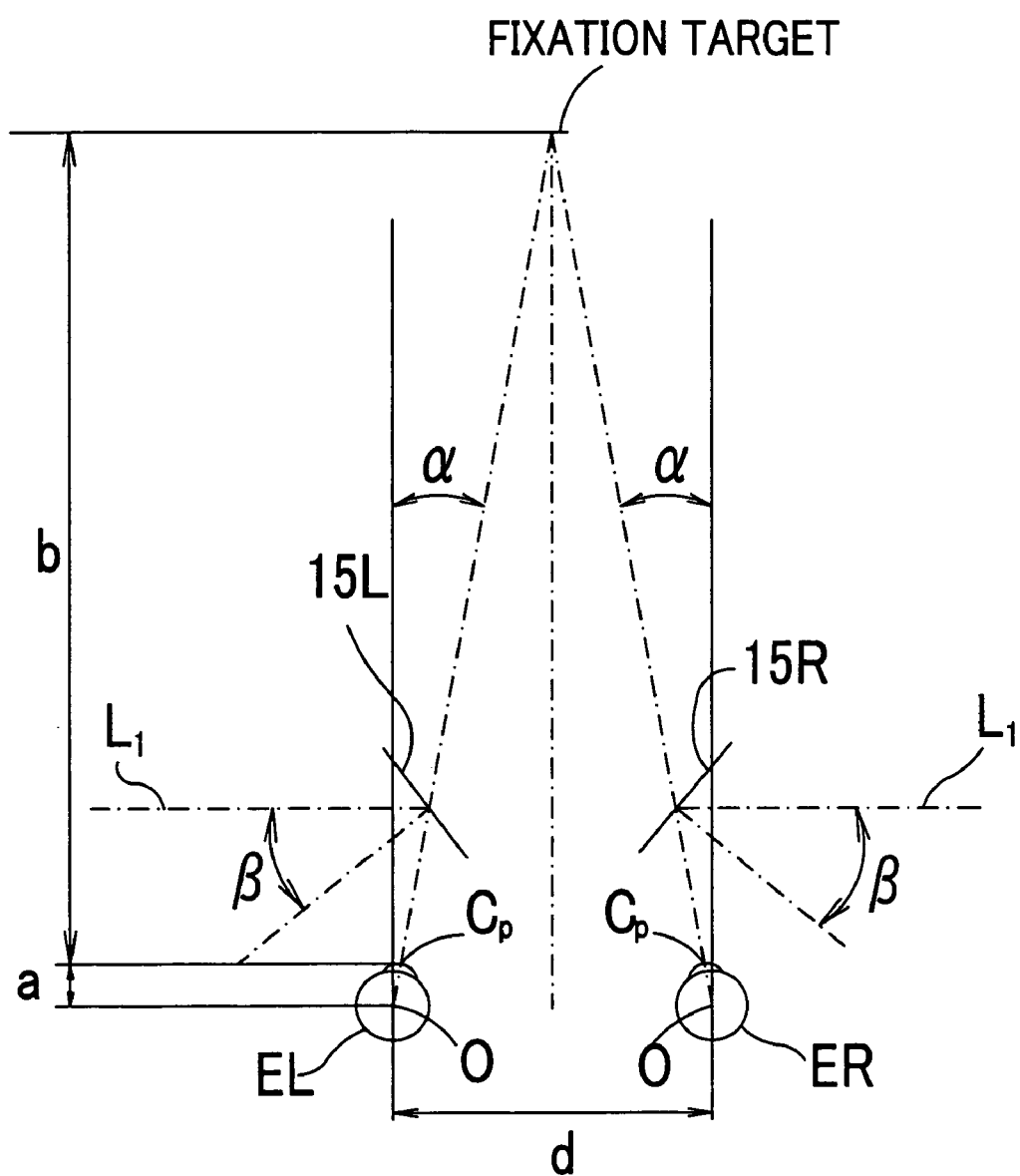
FIG. 4 is a view explaining rotation of right and left movable mirrors according to convergence amounts of right and left eyes.

FIG. 4 is a view explaining the rotation of the mirrors 15R and 15L according to each convergence amount of the eyes ER and EL. Assuming that the distance from a cycloduction point O to a corneal apex Cp of the eye ER (EL) is "a", the distance from the corneal apex Cp to the presenting position of a fixation target is "b", and the pupillary distance between the eyes ER and EL for far vision is "d", the deflection angle α (half of the convergence angle θ) of the visual axis of the eye ER (EL) is:

$$\alpha = \tan^{-1}(d/(2a+2b)).$$

Assuming that the incident angle of the optical axes L1 and L2 to the mirror 15R (15L) at this time is "β", the following expression is given:

$$\beta = (90° - \alpha)/2.$$

The pupillary distance d is obtained based on the detected positional information by the position detecting parts 12R and 12L at the time of completion of alignment of the examination units 10R and 10L in the distance refractive power measurement. Alternatively, a value obtained by a pupillary distance measurement device may be inputted by use of the switch of the switch part 80.

The analysis and control part 70 obtains the rotation amount of the mirrors 15R and 15L for the above respective fixation target presenting positions and causes the motors 16R and 16L to rotate the mirrors 15R and 15L so that each visual axis of the eyes ER and EL is brought in a convergence state according to the presenting position (the presenting distance) of the fixation target, changing the incident angle of the optical axes L1 and L2 to the eyes ER and EL, thereby converging each visual axis of the eyes ER and EL looking the fixation target. In association with this rotation of the mirrors 15R and 15L, the alignment state of the examination units 10R and 10L is adjusted. The adjustment of the alignment state of the examination units 10R and 10L is conducted based on the alignment target images picked up by the image pick-up elements 54R and 54L in the same manner as above.

By changing (moving) the presenting position of the fixation target, variations in refractive power within the time T for each position are acquired. At the same time, variations in pupil size and changes in eye position are acquired (detected) based on each anterior segment image of the eyes ER and EL picked up by the image pick-up elements 54R and 54L. The changes in eye position can be acquired (detected) from changes in center position of the pupil and besides from changes in center position of two infinite target images by the first projecting optical systems. Each acquired (detected) result is stored in the memory 84.

For determining the frequency of occurrence of the high frequency component (HFC) from the variations in refractive power, it is necessary to acquire variations in refractive power at period time shorter than 0.1 second. If it takes long time to analyze the whole ring image, partial information of the ring image may be used for acquisition of the variations. For instance, two coordinates in only a specified meridian direction, e.g., the horizontal meridian direction with reference to the center of the ring image, are detected and the refractive power in that direction is obtained based on the interval between the two coordinates. In case of the eye having astigmatism, it is preferably to correct the refractive power by an amount corresponding to the astigmatism based on the astigmatism information obtained in the distance refractive power measurement.

When the variations in refractive power acquired at each fixation target presenting position and others are stored in the memory 84, the analysis and control part 70 starts the analysis of an accommodative function.

The analysis of the accommodative function is briefly explained. Since refractive power data may be widely different in case the eye blinked, this is removed. Data loss and irregularity due to the blinking are corrected by cubic spline. Then, a frequency analysis is performed by means of a fast Fourier transform (FFT) to calculate a power spectrum. This calculation of a power spectrum is conducted at each of intervals set within the time T (e.g. 20 seconds). Within the time T, the intervals are set to lag behind preceding ones by a predetermined time (e.g., 1 second) and have an equal duration (e.g., 8 seconds). The calculated power spectrum is converted to common logarithms and analyzed. Based on this power spectrum, a mean power spectrum (in dB) in the intervals for high frequency components of 1.0 to 2.3 Hz is determined and evaluated as the "frequency of occurrence of high frequency component" (HFC) of accommodative microfluctuation.

Figure 5:
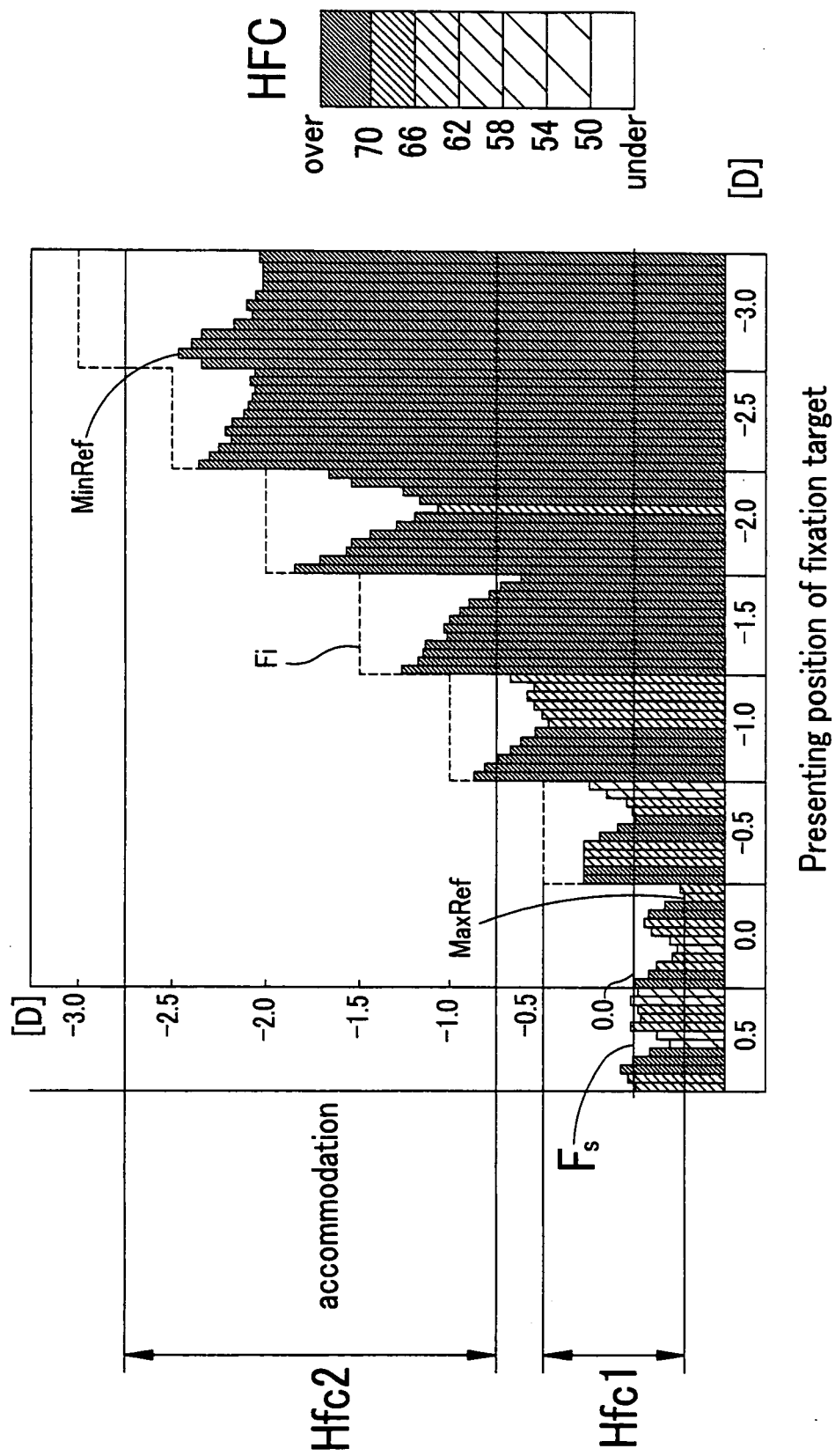
FIG. 5 is an example of a display showing results of analysis of an accommodative function.

FIG. 5 is an example of a analysis result displayed on the monitor 7. This is a display example of the analysis result of one eye. The analysis results of both eyes may be displayed simultaneously on the monitor 7. These analysis results are displayed in terms of three parameters; fixation target presenting position (distance), amount of accommodation response, and HFC, in the form of a three dimensional graph with color cord maps. In this graph, the vertical axis indicates the amount of accommodation response (in D) and the horizontal axis indicates the fixation target presenting position, where variations in the amount of accommodation response corresponding to elapsed times within the time T at each presenting position are graphed in a bar graph. The HFC is color-coded in for example seven levels. For example, an HFC less than 50 is displayed in green, an HFC not less than 70 is displayed in red, and other HFC therebetween is displayed with gradations in color between green through yellow to red. In this figure, a single line FS indicates an S value obtained in the distance refractive power measurement and is shown in association with the amount of accommodation response at each presenting position. A dotted line Fi indicates refractive power obtained by conversion of each presenting position to refractive power.

Figure 6:
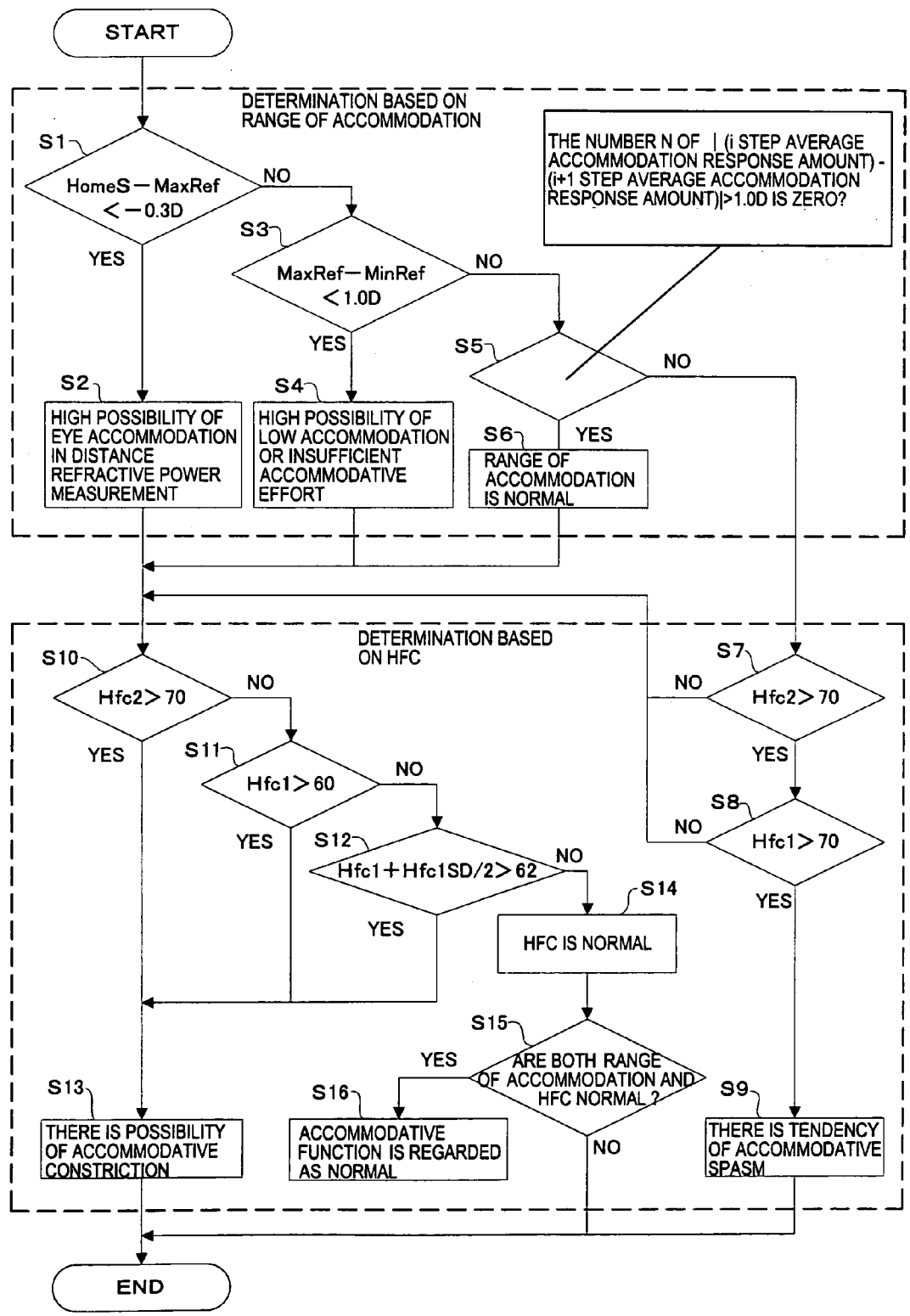
FIG. 6 is a flowchart explaining automatic determination on symptoms of the accommodative function.

Next, the automatic determination of symptoms of the accommodative function is explained (see a flowchart of FIG. 6). This determination is divided roughly into the determination based on the range of accommodation and the determination based on the HFC. The alphabetic signs used in the following explanation mean as follows;

HomeS: Refractive power (S value) acquired in the distance refractive power measurement;
MaxRef: Refractive power on the farthest point side;
MinRef: Refractive power on the nearest point side;
Hfc1: Average HFC in a range from MaxRef to MaxRef−0.75D;
Hfc2: Average HFC in a range from MaxRef−1.0D to MaxRef−3.0;
Hfc1SD: HFC Standard deviation in a range from MaxRef to MaxRef−0.75D.

In FIG. 5, MaxRef is shown in the lowest portion of the accommodative response amount graph, it is +0.25D in this example. MinRef is shown in the highest portion of the accommodative response amount graph, it is −2.50D. In this example, Hfc1 is an average HFC in a range of +0.25D to −0.25D and Hfc2 is an average HFC in a range of −0.75D to −2.75D.

The reason for separating Hfc1 and Hfc2 in the determination based on the HFC is as follows. The resting state of accommodation (a state where ciliary muscle is not working) of a human eye is in −0.75D to about −1.0D from refractive power for a far point. Ciliary muscle works to thin a crystalline lens for the far point side than the accommodation resting state, whereas ciliary muscle works to thicken the crystalline lens for the near point side than the accommodation resting state. Accordingly, Hfc1 is an index for judging a state of the ciliary muscle working to thin the crystalline lens and Hfc2 is an index for judging a state of the ciliary muscle working to thicken the crystalline lens.

A flow of the automatic determination is explained. Firstly, it is determined whether or not a value obtained by subtracting MaxRef from HomeS is smaller (a negative side) than −0.3D (whether or not a difference between HomeS and MaxRef is larger than 0.3D) (step S1). If YES, it is determined that "there is a high possibility that the eye accommodated in the distance refractive power measurement" (step S2). In general, there is an error of the order of 0.25D when the distance refractive power of a human eye is measured. Considering the error, a difference of 0.3D is set as a determination condition (a reference value). If NO in step S1, it is determined whether or not a value (a variation range of refractive power) obtained by subtracting MinRef from MaxRef is smaller than 1.0D (whether or not a difference between MaxRef and MinRef is smaller than 1.0D) (step S3). If YES, which shows that the variation in accommodation response amount is small even when the presenting position of the fixation target is changed to the near position, it is determined that "the range of accommodation is low or there is a high possibility that accommodative effort was insufficient" (step S4). This corresponds to the case of a presbyopic eye. If No in step S3, found is an absolute value of a value obtained by subtracting an average refractive power (range of accommodation) of an i+1 step from an average refractive power (range of accommodation) of a certain i step of the presenting position of the fixation target changed (moved) in steps of 0.5D. The absolute value is a difference between the average refractive power of the i step and the average refractive power of the i+1 step. It is determined whether or not the number N of the absolute value that exceeds 1.0D is at least one or more (step S5). This 1.0D as the determination condition (the reference value) is set as a larger value than 0.5D which is a step for changing (moving) the presenting position of the fixation target. If NO in step S5, which shows accommodative spasm may have occurred, the flow advances to steps S7 and S8 for determining the presence/absence of accommodative spasm based on the HFC. In the present embodiment, the changing (moving) step i of the presenting position of the fixation target used for the determination in step S5 is set at 1 to 5 steps on the far point side. The further steps on the near point side are excluded. This is made to remove the case where, when the presenting position of the fixation target comes to a near position to some degree, a person who has a small accommodative range cannot clearly see the fixation target and likely abandons, causing the range of accommodation to lower. If YES in step S5, it is determined that the range of accommodation is normal (step S6). Each determination condition is not limited to these values.

After the determination based on the range of accommodation, the determination based on the HFC follows. If NO in step S5, the presence/absence of accommodative spasm is determined based on the HFC (step S7). Firstly, it is determined whether or not Hfc2 is a higher value than an HFC value 70 (dB). If YES, it is further determined whether or not Hfc1 is a higher value than the HFC value 70 (dB) (step S8). If YES in step S8, it is determined that the HFC is a higher value with respect to the presenting position of the fixation target other than a visual distance regarded as an accommodation resting state and "there is a tendency of accommodative spasm" (step S9).

If YES in any one of steps S1, S3, and S5 or if NO in step S7 or S8, the presence/absence of accommodation constriction is determined based on the HFC. It is first determined whether or not Hfc2 is a higher value than the HFC value 70 (dB) (step S10). If NO, it is further determined whether or not Hfc1 is a higher value than the HFC value 60 (dB) (step S11). If NO in step S11, it is further determined whether or not a value obtained by adding Hfc1 and Hfc1SD/2 is a higher value than an HFC value 62 (step S12). If YES in any one of steps S10, S11, and S12, it is determined that "there is a possibility of accommodative constriction" (step S13). In step S12, even when the average HFC in a range from MaxRef to MaxRef−0.75D does not show a high value, it is determined that "there is a possibility of accommodative constriction" if a certain high value is given in consideration of a standard deviation. If NO in step S12, the HFC is determined as being normal (step S14). It is then determined in the following step S15 whether or not the range of accommodation was also normal. If YES, it is determined that "the accommodative function is considered as normal" (step S16).

Each determination result in the above steps S2, S4, S6, S9, S13, and S16 is displayed on the monitor 7 as a message or the like in addition to the graphical display in FIG. 5 to inform the examiner thereof. Such display of the determination results, the examiner can accurately grasp the symptom of accommodative function and easily diagnose. Further, differences in reading among examiners are eliminated, and determination errors, a failure to notice of symptoms, and so on can be reduced.

Not only determining the presence/absence of accommodative constriction and the presence/absence of accommodative spasm but also determining respective degrees in steps make it possible to further facilitate diagnosis. For instance, the degree of accommodative constriction is determined in three steps; severe accommodotonia, accommodotonia, accommodotonia tendency, according to the values such as Hfc1 and Hfc2 (in the order of higher values of the HFC) in the above steps S10, S11, and S12. The degree of accommodative spasm is determined in three steps according to the number N in step S5; severe accommodative spasm if the number N is five or more, moderate accommodative spasm if the number N is three or four, and slight accommodative spasm if the number N is one or two.

In the present apparatus, in addition to the determination of the symptoms of accommodative function, determination is conducted based on the pupil size, eye position, and convergence state. These are explained below.

In the accommodative function examination, at the time of acquiring variations in refractive power at each presenting position of the fixation target, changes in pupil size and changes in eye position are acquired (detected) based on the picked-up anterior segment image. When an amount of change and a speed of change are larger than a permissible range determined from an acquired (detected) result about a normal eye, it is determined that the eye may have some abnormalities or be fatigable. A message to that effect is displayed on the monitor 7.

The changes in eye position can be utilized for the determination of presence/absence of nystagmus and others. The changes in pupil size can be utilized for the determination of stability of fixation.

Since the changes in positions of both eyes can be acquired (detected) at the same time, the changes in convergence amount can also be acquired (detected). The changes in convergence amount are acquired (detected) based on the positional information of the examination units 10R and 10L in the X-, Y-, and Z-directions and the rotational information of the mirrors 15R and 15L. Whether the optical axes L1 and L2 coincide with the visual axis is detected based on the positional relation between the alignment target image and the pupil. Each examination unit 10R, 10L is moved in the X-, Y-, Z-directions and also the mirrors 15R and 15L are rotated so that the center position of the alignment target image comes to the center position of the pupil. Alternatively, the changes in convergence amount is acquired (detected) based on a difference between a normal convergence amount calculated according to the presenting position (the presenting distance) of the fixation target as mentioned above and an actual convergence amount. Further, in the same manner as above, when the change amount and change speed of the convergence amount vary largely than a permissible range (which can be determined based on the acquired (detected) result about the normal eye), it is determined that the eye has convergence function errors such as convergence spasm, convergence response disorder, and others. A message to that effect is displayed on the monitor 7. Furthermore, the convergence normally changes according to the changes in the presenting position of the fixation target. However, if the convergence follows with a large delay or without stability, there may be convergence function errors. The movements of right and left eyes can be not only merely obtained as the convergence amount but also separately acquired (detected). Thus, it is possible for example to determine a difference in converging motion between the right and left eyes when the fixation target comes to the near position. Moreover, convergent accommodation can also be acquired (detected), which facilitates more appropriate diagnosis.

In the above explanation, the values used in the determination of symptoms of accommodative function (e.g., the values for a range such as Hfc1, Hfc2, and others, the values for determination of the presence/absence of accommodative constriction and accommodative spasm, and others) are merely examples and not limited to them.

The eye refractive measuring optical system is not limited to the above one but may be selected from various well known types. Similarly, the fixation target presenting optical system is not limited to the above one but may be selected from various well known types.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An ocular accommodative function examination apparatus for examining an accommodative function of an examinee's eye, comprising:
    a fixation target presenting optical system which presents a fixation target at a presenting position to the eye, the presenting position being changeable in a direction of a visual axis of the eye;
    a refractive power measuring optical system which measures refractive power of the eye and includes a light projecting optical system which includes a light source and projects examination light to a fundus of the eye and a light receiving optical system which includes a light receiving element and receives the examination light reflected from the fundus;
    an analysis part which acquires variation in the refractive power of the eye gazing at the fixation target at a certain presenting position within a predetermined time based on output of the light receiving element, and determines the accommodative function including a range of accommodation and HFC (a frequency of occurrence of a high frequency component of accommodative microfluctuation) of the eye based on an acquired result; and
    an output part which outputs a result determined by the analysis part,
    wherein the analysis part determines presence/absence of accommodative constriction and presence/absence of accommodative spasm based on the determined range of accommodation and HFC.

2. The ocular accommodative function examination apparatus according to claim 1, wherein the analysis part determines the presence/absence of the accommodative constriction and the presence/absence of the accommodative spasm based on the number of times N that a difference between the ranges of accommodation at two presenting positions exceeds a reference value.

3. The ocular accommodative function examination apparatus according to claim 2, wherein the analysis part determines the presence/absence of the accommodative constriction and the presence/absence of the accommodative spasm based on the HFC in a first presenting position range on a far point side and the HFC in a second presenting position range on a near point side.

4. The ocular accommodative function examination apparatus according to claim 2, wherein the analysis part determines a degree of the accommodative constriction in steps based on the HFC and determines a degree of the accommodative spasm in steps based on the number of times N.

5. The ocular accommodative function examination apparatus according to claim 1 further comprising a pupil size detecting part which detects pupil size of the eye,
   wherein the analysis part acquires change in the pupil size based on a result of the detection of the pupil size and, based on a result thereof, determines presence/absence of abnormality of the eye.

6. The ocular accommodative function examination apparatus according to claim 1 further comprising a position detecting part which detects a position of the eye,
   wherein the analysis part acquires change in the position of the eye based on a result of the detection of the position and, based on a result thereof, determines presence/absence of abnormality of the eye.

7. The ocular accommodative function examination apparatus according to claim 1 further comprising a convergent state detecting part which detects a convergent state of the eye,
   wherein the analysis part acquires change in the convergent state based on a result of detection of the convergent state and, based on a result thereof, determines presence/absence of abnormality of the eye.

8. An ocular accommodative function examination apparatus for examining an accommodative function of an examinee's eye, comprising:
   a fixation target presenting optical system which presents a fixation target at a presenting position to the eye, the presenting position being changeable in a direction of a visual axis of the eye;
   a refractive power measuring optical system which measures refractive power of the eye and includes a light projecting optical system which includes a light source and projects examination light to a fundus of the eye and a light receiving optical system which includes a light receiving element and receives the examination light reflected from the fundus;
   a right eye examination unit and a left eye examination unit in each of which the fixation target presenting optical system and the refractive power measuring optical system are disposed;
   a moving part which moves each examination unit;
   a position detecting part which detects each position of a right eye and a left eye;
   a control part which controls the moving part based on the detected positions;
   an analysis part which acquires variation in the refractive power of the eye gazing at the fixation target at a certain presenting position within a predetermined time based on output of the light receiving element, and determines the accommodative function including a range of accommodation and HFC (a frequency of occurrence of a high frequency component of accommodative microfluctuation) of the eye based on an acquired result; and
   an output part which outputs a result determined by the analysis part.

9. The ocular accommodative function examination apparatus according to claim 8 further comprising a pupillary distance acquiring part which acquires a pupillary distance between the right eye and the left eye,
   wherein the control part controls the moving part based on the acquired pupillary distance.

10. The ocular accommodative function examination apparatus according to claim 8 further comprising converging means which changes an incident angle of an optical axis of the fixation target presenting optical system for the right eye with respect to the right eye and changes an incident angle of an optical axis of the fixation target presenting optical system for the left eye with respect to the left eye so that each visual axis of the right and left eyes is brought in a convergence state according to the presenting position of the fixation target.

11. The ocular accommodative function examination apparatus according to claim 10, wherein the control part controls the moving part based on change of each incident angle.

12. The ocular accommodative function examination apparatus according to claim 10, wherein the converging means includes a movable mirror disposed in each of the examination units.

13. The ocular accommodative function examination apparatus according to claim 8, wherein the position detecting part includes a projecting optical system which projects an alignment target to the eye and a detecting optical system which detects the projected alignment target, the position detecting part is disposed in each of the examination unit to detect a relative position of the right eye with respect to the right eye examination unit and detects a relative position of the left eye with respect to the left eye examination unit.

14. The ocular accommodative function examination apparatus according to claim 8, wherein the analysis part determines presence/absence of accommodative constriction and presence/absence of accommodative spasm based on the determined range of accommodation and HFC.

* * * * *